United States Patent [19]

Dhaon et al.

[11] Patent Number: 5,312,985
[45] Date of Patent: May 17, 1994

[54] METHOD OF SYNTHESIZING THE PRECURSOR PYRUVAMIDE

[75] Inventors: Madhup K. Dhaon, Mundelein; John A. Houbion, Vernon Hills, both of Ill.

[73] Assignee: Abbott Laboratories, Abbott Park, Ill.

[21] Appl. No.: 43,699

[22] Filed: Apr. 8, 1993

Related U.S. Application Data

[62] Division of Ser. No. 868,891, Apr. 16, 1992, Pat. No. 5,256,697.

[51] Int. Cl.$^5$ ............................................. C07C 231/02
[52] U.S. Cl. ..................................... 564/143; 562/843
[58] Field of Search ........................ 562/843; 564/143

[56] References Cited

U.S. PATENT DOCUMENTS

| | | | |
|---|---|---|---|
| 3,838,027 | 9/1974 | Berntsson | 204/74 |
| 4,197,316 | 4/1980 | Yu et al. | 424/317 |
| 4,296,127 | 10/1981 | Walser | 424/319 |
| 4,351,835 | 9/1982 | Stanko | 514/251 |
| 4,548,937 | 10/1985 | Stanko | 514/251 |
| 4,734,276 | 3/1988 | Ziegler | 233/265 |
| 4,874,790 | 10/1989 | Stanko | 514/557 |
| 5,053,527 | 10/1991 | Christidis et al. | 560/174 |
| 5,089,492 | 2/1992 | Gerling et al. | 514/210 |

OTHER PUBLICATIONS

"Transamination of Peptides", Dixon, *Biotechnology Journal*, vol. 92, pp. 661–666, (1964).
"Prevention of Alcohol–Induced Fatty Liver By Natural Metabolites and Riboflavin", Stanko et al., *Journal of Laboratory and Clinical Medicine*, Feb. 1978.
"A Facile Preparation of Primary Carboxamides", Pellegata et al., *Communications*, May 1985, pp. 517–519.
"Inhibition of Lipid Accumulation and Enhancement of Energy Expenditure by the Addition of Pyruvate and Dihydroxyacetone to a Rat Diet", Stanko et al. *Metabolism*, vol. 35, No. 2, Feb., 1986, pp. 182–186.

*Primary Examiner*—Richard L. Raymond
*Attorney, Agent, or Firm*—Lonnie R. Drayer; Donald O. Nickey

[57] ABSTRACT

A method for administering pyruvate is disclosed which comprises administering a therapeutically effective amount of a pyruvate precursor to a mammal in the form of pyruvamide or a pyruvyl-amino acid. The pyruvyl-amino acid is preferably selected from the group comprising pyruvyl-glycine, pyruvyl-alanine, pyruvyl-leucine, pyruvyl-valine, pyruvyl-isoleucine, pyruvyl-phenylalanine, pyruvyl-proline and pyruvyl-sarcosine, and their amides and esters as well as their salts. Associated with the administration of a pyruvate precursor to a mammal in accordance with this invention are improved insulin resistance, lower fasting insulin levels, and reduced fat gain. Novel methods of synthesizing several pyruvate precursors are also disclosed.

2 Claims, 5 Drawing Sheets

METHOD OF SYNTHESIZING THE PRECURSOR PYRUVAMIDE

This is a divisional of application Ser. No. 07/868,891 filed on Apr. 16, 1992, now U.S. Pat. No. 5,256,697.

TECHNICAL FIELD

The present invention relates generally to a method of administering pyruvate to mammals, and to methods of synthesizing non-salt precursors to pyruvate.

BACKGROUND ART

Obesity is a multifactorial disease which affects upwards of 25% of the adult population in the United States of America. It is estimated that in the U.S.A. between 34–50 million adults are obese, with at least 5 million of those adults receiving medical treatment for their obesity. The etiology of obesity can range from simple overeating to severe hormonal imbalance. However, the great majority of obesity is probably due to a complex relationship between the many factors that regulate energy intake and utilization.

Teleologically, obese individuals may be better prepared for survival in time of limited food supply because of their ability to utilize energy in a more efficient manner. However, given that there is almost an unlimited food supply in the U.S.A., this efficiency of energy utilization probably leads to obesity. Furthermore, obesity is associated with an increased risk of cardiovascular disease, an increased risk of Type II diabetes, an increased risk of coronary artery disease, and other chronic diseases. For example, it is believed that in the U.S.A. there are over 6 million diagnosed cases of obese Type II diabetes, with an estimated 4 million cases being undiagnosed.

Given the large obese population and the associated problems, the area of obesity research and product development for the management of obesity has been explored, yet the problem remains. U.S. Pat. No. 4,351,835 teaches a method for preventing body fat deposition in mammals by oral administration of a mixture of pyruvate and dihydroxyacetone (DHA).

Subsequent additional research with rats investigated the effect of pyruvate and DHA under normal dietary conditions. In that study, rats were fed either a controlled diet or an experimental diet in which part of the carbohydrates were replaced with a 1:1 mixture of pyruvate and DHA, which mixture constituted 15% of the total caloric intake. Rats which received the experimental diet gained less weight, and had greater rates of heat production and energy expenditure than rats receiving a control diet. The experimental diet reduced body fat content by 32% without any significant effect on either protein or water content.

Similarly, in another study, Type II diabetic humans were fed 56 grams of pyruvate and OHA in a 1:1 mixture for seven days, during which time period glucose tolerance and turnover were measured. Reductions in fasting blood glucose concentration and peak glucose concentration after a glucose tolerance test were observed.

Yet another study assessed the relative effectiveness of pyruvate and DHA. In that study, obese Zucker rats were placed in one of four diet groups. One diet was a control and each of the other diets featured a semi-purified rat diet with only one of the following features: (a) 6% pyruvate, (b) 6% DHA, or (c) 6% pyruvate/DHA (1:1). A number of physiologic variables were measured. The conclusion of the study was that generally changes due to the addition of DHA or pyruvate/DHA to the diet were not as great as changes due to the addition of only pyruvate. In fact, often the changes due to the addition of DHA or pyruvate/DHA could either be attributed to feed restriction or to the pyruvate in combination.

Finally, U.S. Pat. No. 4,548,937 discloses a method for minimizing weight gain by adding pyruvate to the diet.

Based on the above studies, the experimental data indicated that pyruvate was an efficacious compound in altering metabolic variables in rats. Pyruvate, also known as pyruvic acid, is a common metabolite of the body.

A problem exists in administering effective dosages of pyruvate to humans in that heretofore the only ways to supply pyruvate have been in the form of a liquified pyruvic acid or in the form of the mineral salts of pyruvate, for example via sodium, potassium or calcium salts. These salts are organoleptically poor, as is tolerance of these salts. Furthermore, in humans the amount of these salts required to obtain the proper dosage of pyruvate for maximal effect raises the electrolyte level of the recipient to 2–6 times the safe and adequate recommended level when given as a supplement to a typical diet. With respect to the liquid pyruvic acid, the liquid is very acidic and results in the body literally being burned. Attempting to solve the acidity problem through dilution results in the human body being unable to ingest acceptable levels of pyruvate.

It is thus apparent that the need exists for an improved method of administering pyruvate to humans. It is also apparent that the need exists for an improved method of synthesizing a hydrolyzable precursor for pyruvate, other than in the form of a pyruvate salt.

DISCLOSURE OF THE INVENTION

There is disclosed a method for administering pyruvate to mammals, which method comprises administering a therapeutically effective amount of a pyruvate precursor in the form of pyruvamide or a pyruvyl-amino acid. More preferably the pyruvate precursor constitutes between 2%–20% by weight of the diet of the mammal.

There is also disclosed a method for improving insulin resistance in a mammal, as measured by a fasting blood glucose tolerance test, which method comprises administering a therapeutically effective amount of a pyruvate precursor in the form of a pyruvyl-amino acid prior to performing a fasting blood glucose tolerance test, such that it requires a reduced level of insulin to maintain blood glucose levels in the fasting blood glucose tolerance test than is exhibited in the absence of the prior administration of the pyruvate precursor. More preferably the pyruvate precursor constitutes between 2%–20% by weight of the diet of the mammal.

There is also disclosed a method for reducing fat deposition in mammals, which method comprises administering a therapeutically effective amount of a pyruvate precursor in the form of a pyruvyl-amino acid.

There are also disclosed methods of synthesizing the pyruvate precursors pyruvamide, pyruvyl-glycine, pyruvyl-alanine, pyruvyl-valine, pyruvyl-leucine, and pyruvyl-isoleucine.

One aspect of the invention provides an effective method for administering pyruvate to mammals.

Yet another aspect of the invention resides in a relatively easy and cost effective method for synthesizing a pyruvate precursor, other than in the form of a salt.

Other aspects and advantages of the instant invention will be apparent from the following description, examples, and the appended claims.

DETAILED DESCRIPTION OF THE INVENTION

The present invention is concerned with a dietary supplement which can be utilized by obese or overweight mammals, as well as mammals having Type II diabetes. The present invention is also concerned with the synthesis of a precursor for pyruvate, other than in the form of a salt.

Although at this time pyruvate theoretically appears to be the most efficacious compound in addressing obesity and problems associated with Type II diabetes, the utility of pyruvate in humans in the clinical management of Type II diabetes or obesity has been limited by the elevated mineral load associated with pyruvate salts, which until this time were the only practical method of supplying pyruvate to the body. Pyruvate can also be supplied as a liquid acid, but it is so acidic that it must be diluted. When the liquid acid is diluted sufficiently to be tolerable, it requires too large a volume of liquid to be consumed in order to obtain a sufficient ingestion of pyruvate.

Table I illustrates the raised electrolyte levels associated with the generation of an effective dose (28 grams) of pyruvate in the form of pyruvate salts, with the salts being used either alone or in combination.

TABLE I

| 28 g Pyruvate | Na+ | K+ | Ca++ |
|---|---|---|---|
| Single salt, mg | 7,000 | — | — |
| Single salt, mg | — | 12,560 | — |
| Single salt, mg | — | — | 6,400 |
| Combination*, mg | 3,500 | — | 3,200 |
| Combination*, mg | — | 6,300 | 3,200 |
| Combination*, mg | 2,330 | 4,180 | 2,140 |
| ESADDI** range, mg | 1100–3300 | 1875–5625 | 1,200 |

*Each salt is added as an equal proportion of the total 28 grams of pyruvate.
**Estimated Safe and Adequate Daily Dietary Intake in the RDA 10th edition.

As can be seen from Table I, the electrolyte level is raised to between 2-6 times the level recommended in humans, regardless of how the pyruvate salts are ingested.

In order to dispense or generate pyruvate in mammals, a unique, method has been proposed which resulted in a unique synthesis for preparing pyruvamide, a hydrolyzable precursor of pyruvate. Earlier syntheses of pyruvamide has been by hydrolysis of pyruvonitrile, by the acid hydrolysis of lantacidin A, or by the permanganate oxidation of lactamide.

The unique proposed synthesis of pyruvamide associated with this invention utilized the generation of pyruvyl chloride in situ from sodium pyruvate and thionyl chloride or oxalyl chloride. The pyruvyl chloride was then reacted with 1,1,1,3,3,3-hexamethyldisilazane (HMDS) at a temperature of 0°–40° Centigrade, followed by treatment with methanol in the presence of a suitable solvent such as dichloromethane (DCM), tetrahydrofuran (THF), or dimethylformamide (DMF) to generate the pyruvamide. The yield of pyruvamide was in the range of 50-80%. It was then discovered that higher yields and less colored by-products were formed by replacing the thionyl chloride with oxalyl chloride. This improved the method of obtaining the pyruvyl chloride intermediate.

The pyruvate analog, pyruvamide, and its unique synthesis were believed to have solved the problem as to a usable pyruvate source, since this particular synthesis did not require ultimate ingestion of a pyruvate mineral salt. Rather surprisingly, in subsequent studies with rats, it was found that the rats apparently did not exhibit a tolerance for pyruvamide at the dosage used. Rats in that particular test group consumed insignificant quantities of food, and while the rats lost appreciable body weight, this was believed to be due to the consumption of an insignificant quantity of food and not due to any desirable reasons. The reason for the rats' surprising aversion to the diet comprising pyruvamide was not completely understood, and required further study and testing.

Since it was initially determined that pyruvamide is not a preferred pyruvate analog, other pyruvate precursors were investigated. It was then found that other hydrolyzable, non-salt, pyruvate precursors could be synthesized. For example, an improved synthesis of pyruvyl-glycine via a benzyl ester protection method, was discovered. The traditional method of synthesis of pyruvyl-glycine involves reacting phosphorous oxychloride or p-toluene sulfonyl chloride with pyravic acid to yield pyruvyl chloride. The pyruvyl chloride formed using the traditional synthesis is then reacted with glycine benzyl ester hydrochloride to form pyruvyl-glycine benzyl ester, or with glycine in pyridine to yield pyruvyl-glycine. The yield of pyruvyl-glycine benzyl ester was about 35%, and the yield of pyruvyl-glycine was about 12%.

The improved method of synthesis involves the reaction of sodium pyruvate with thionyl chloride or preferably with oxalyl chloride to form pyruvyl chloride. The pyruvyl chloride is then reacted with glycine benzyl ester hydrochloride to form the pyruvyl-glycine benzyl ester, with a yield of about 85%. The pyruvyl-glycine benzyl ester then undergoes hydrogenolysis to obtain pyruvyl-glycine with a yield of about 90%. It can be readily appreciated that the ultimate yield of pyruvyl-glycine using this improved method is substantially higher than the yield associated with the traditional method of synthesis. This improved method is set forth below.

Preferably in this method of synthesis, the thionyl chloride or oxalyl chloride is added to a suspension of sodium pyruvate to yield the pyruvyl chloride to which is added the of glycine benzyl ester hydrochloride. The resulting slurry is cooled during the addition of N-methylmorpholine solution to yield a pyruvyl-glycine benzyl ester. The yielding of the pyruvyl-glycine benzyl ester occurs after warming, the addition of water, separation, washing, drying, evaporation, precipitation, filtering, and drying again. The pyruvyl-glycine benzyl ester is then charged in a hydrogen pressure vessel in a solvent and a palladium on carbon catalyst, with the hydrogen pressure being approximately 60 psi such that hydrogen is digested whereby following filtering, concentration, precipitation, filtering, and drying there is yielded pyruvyl-glycine.

More preferably the thionyl chloride or oxalyl chloride is added to a mechanically stirred suspension of sodium pyruvate in dichloromethane whereby a gas is evolved and pyruvyl chloride is yielded. The pyruvyl chloride is cooled during the dropwise addition of glycine benzyl ester solution to yield pyruvyl-glycine benzyl ester following the warming to room temperature, the addition of water, separation, washing with diluted hydrochloric acid and brine, drying with magnesium sulfate, evaporation of the dichloromethane, precipitation, filtering and drying again. The pyruvyl-glycine benzyl ester is then charged in a hydrogen pressure vessel with ethyl acetate and 4% to 20% palladium on carbon, with the hydrogen pressure being approximately 40-150 psi, such that hydrogen is digested whereby following warming, filtering, concentration, precipitation, filtering and drying there is yielded pyruvyl-glycine.

For example to synthesize the pyruvyl-glycine benzyl ester set forth above, a stirred suspension of glycine benzyl ester hydrochloride (182 g, 0.9 mol) in dichloromethane (500 ml) is added drop wise at room temperature to N-methlymorpholine (220 ml, 2 mol). After approximately 2 hours, the solution is refrigerated and the precipitated salt is filtered and discarded prior to use. Additionally, to a mechanically stirred suspension of sodium pyruvate (110 g, 1 mol) in dichloromethane (1 L) is added oxalyl chloride (110 ml, 1 mol) in one portion. The evolution of gas subsides after approximately 5 hours. The pale yellow slurry is kept under a blanket of nitrogen and cooled to between −20° and −30° Centigrade during the dropwise addition of the glycine benzyl ester hydrochloride solution prepared above. The slurry is then warmed to room temperature. Water (1 L) is added. The lower organic layer is separated and washed with diluted HCl (3 times with 500 ml), brine (2 times with 250 ml), and finally dried with magnesium sulfate. The dichloromethane is then evaporated and finally when precipitation begins, heptane is slowly added to increase productivity. The sandy solid is filtered and dried to a constant weight.

A hydrogen pressure vessel is charged with the pyruvyl-glycine benzyl ester (120 g, 0.51 mol), ethyl acetate (480 ml), and 4% palladium on carbon (12 g, 10% by weight). Hydrogen pressure is adjusted to approximately 60 psi, the temperature to approximately 40° Centigrade and the reagents stirred until a stoichiometric amount of hydrogen is digested. The solution is then filtered through 1.5 micron glass fiber filter and concentrated. When product starts precipitating, heptane is again added to increase productivity. The precipitate is filtered and dried to a white solid of constant weight which is pyruvyl-glycine.

A method of synthesizing pyruvyl-alanine or pyruvyl-glycine according to the invention comprises the steps of reacting sodium pyruvate with oxalyl chloride to yield pyruvyl chloride, then reacting pyruvyl chloride with a suspension of alanine trimethylsilyl ester hydrochloride to yield a pyruvyl-alanine trimethylsilyl ester and then subjecting the pyruvyl-alanine trimethylsilyl estertohydrolysis to yield pyruvyl-alanine. The pyruvyl-alanine synthesized via the method set forth above serves as a pyruvyl-amino acid pyruvate precursor.

A method of synthesizing pyruvyl-valine according to the invention comprises the steps of reacting sodium pyruvate with oxalyl chloride to yield pyruvyl chloride, then reacting the pyruvyl chloride with a suspension of valine trimethylsilyl ester hydrochloride to yield pyruvyl-valine trimethylsilyl ester and then subjecting the pyruvyl-valine trimethylsilyl ester to hydrolysis to yield pyruvyl-valine. The pyruvyl-valine synthesized via the route set forth above serves as a pyruvyl-amino acid pyruvate precursor.

A method of synthesizing pyruvyl-leucine according to the invention comprises the steps of reacting sodium pyruvate with oxalyl chloride to yield pyruvyl chloride, then reacting the pyruvyl chloride with a suspension of leucine trimethylsilyl ester hydrochloride to yield a pyruvyl-leucine trimethylsilyl ester and then subjecting the pyruvyl leucine trimethylsilyl ester to hydrolysis to yield pyruvyl-leucine. The pyruvyl-leucine synthesized via the route set forth above serves as a pyruvyl-amino acid pyruvate precursor.

A method of synthesizing pyruvyl-isoleucine according to the invention the steps of reacting sodium pyruvate with oxalyl chloride to yield pyruvyl chloride, then reacting the pyruvyl chloride with a suspension of isoleucine trimethylsilyl ester hydrochloride to yield pyruvyl-isoleucine trimethylsilyl ester and then subjecting the pyruvyl-isoleucine trimethylsilyl ester to hydrolysis to yield pyruvyl-isoleucine. The pyruvyl-isoleucine synthesized via the method set forth above serves as a pyruvyl-amino acid pyruvate precursor.

A method of synthesizing pyruvyl-phenylalanine according to the invention comprises the steps of reacting sodium pyruvate with oxalyl chloride to yield pyruvyl chloride, then reacting pyruvyl chloride with a suspension of phenylalanine trimethylsilyl ester hydrochloride to yield pyruvyl-phenylalanine trimethylsilyl ester and then subjecting the pyruvyl-phenylalanine trimethylsilyl ester to hydrolysis to yield pyruvyl-phenylalanine. The pyruvyl-phenylalanine synthesized via the route set forth above serves as a pyruvyl-amino acid pyruvate precursor.

A method of synthesizing the pyruvate precursor pyruvamide, in accordance with the invention comprises the steps of preparing pyruvyl chloride by reacting sodium pyruvate with thionyl chloride or oxalyl chloride to yield pyruvyl chloride, and reacting the pyruvyl chloride with 1,1,1,3,3,3-hexamethyldisilazane at a temperature of 0°-40° Centigrade, followed by treatment with methanol in the presence of a solvent to generate pyruvamide. Preferably the solvent is selected from the group consisting of, but not limited to, dichloromethane, acetonitrile, tetrahydrofuran and dimethylformamide.

Other pyruvate analogs were synthesized, for example with the improved method of synthesis having oxalyl chloride substituted for phosphorous oxychloride or thionyl chloride. The other steps in the syntheses of the other analogs correspond to the steps in the synthesis of the pyruvyl-glycine. While pyruvyl-amino acid precursors comprising alanine, valine, leucine, isoleucine, and phenylalanine could be synthesized using the benzyl ester hydrochloride of the particular amino acid, it was discovered that a preferable synthesis involved their substitution by the trimethylsilyl esters of the respective amino acid.

The most preferred method of synthesizing pyruvyl-glycine will now be described. This method employees inexpensive starting materials, is a one-step synthesis, and has a productivity level that is similar to or superior to the other methods disclosed herein.

In an example of a first embodiment of this most preferred method of synthesizing pyruvyl-glycine a 2L flask (stirrer, condenser, nitrogen) was charged with glycine (15 g, 0.2 mol), anhydrous tetrahydrofuran (400 mL) and trimethylsilyl chloride (22 g, 0.2 mol). The reactants were stirred at reflux for 4 hours. The solution was then cooled to 0° C. in a cooling bath. Separately, to sodium pyruvate (22 g, 0.2 mol) in methylene chloride (400 mL) at 0° C. was added dropwise a solution of oxalyl chloride (26 g, 0.2 mol) in methylene chloride (40 mL). The slurry was then stirred at 25° C. for 2 hours under a blanket of nitrogen. The precipitated sodium chloride was filtered off and the filtrate was added to the above solution of glycine trimethylsilyl ester at 0° C. The condenser was replaced by an addition funnel and a solution of propylene oxide (23 g, 0.4 mol) in methylene chloride (50 mL) was added dropwise at 0° C. The reaction mixture was then stirred to 25° C. over a 2 hour period until clear. Methanol (80 mL) was added at once and the solvents were evaporated. The solid residue (36 g) was recrystallized from ethyl acetate/heptane to a tan solid, mp 86°–7° C. (17 g, 59%.).

In an example of a second embodiment of this most preferred method of synthesizing pyruvyl-glycine a 2L flash (stirrer, condenser, nitrogen) was charged with glycine (15 g, 0.2 mol), anhydrous dioxane (400 mL) and trimethylsilyl chloride (22 g, 0.2 mol). The reactants are stirred at reflux for 4 hours. The solution is then cooled to 0° C. in an ice bath. In a separate flask, oxalyl chloride (26 g, 0.2 mol) is added to sodium pyruvate (22 g, 0.2 mol) in ethyl acetate (400 mL) at 0° C. The slurry was stirred at 25° C. for 2 hours under a blanket of nitrogen. The precipitated sodium chloride was filtered off and the filtrate was added to the above solution of glycine trimethylsilyl ester at 0° C. The condenser was replaced by an addition funnel and a solution of propylene oxide (23 g, 0.4 mol) in ethyl acetate (50 mL) was added dropwise at 0° C. The reaction mixture was then stirred at 40° C. for 2 hours and overnight at 20° C. Methanol (80 mL) was added at once and the solvents were evaporated. The solid residue (34 g) was recrystallized from ethyl acetate/heptane to a tan solid, mp 87° C. (22 g, 76%).

The most preferred one-step synthesis of pyruvyl-glycine comprises charging a 2L flask (air stirrer, condenser, nitrogen inlet) with glycine (15 g, 0.2 mol), anhydrous acetonitrile (ACN)(500 mL) and trimethylsilyl chloride (30.5 mL, 0.24 mol). The reactants are stirred at reflux for 3 hours. The clear turbid solution is then cooled to 5° C. in an ice bath and propylene oxide (100 mL) is added at once. In a separate flask, oxalyl chloride (21 mL, 0.24 mol) is added to sodium pyruvate (24.2 g, 0.22 mol) in ACN (500 mL) at 0° C. with vigorous degassing. The solution is stirred at 25° C. for 3 hours under a blanket of nitrogen. The slurry is cooled to 5° C. and added in one portion to the above trimethylsilyl ester solution at 5° C. The sodium chloride is not filtered off at this stage. The slurry is stirred at 5° C. for about 2 hours and then warmed to 25° C. and held overnight. Methanol (80 mL) is added at once, the salts are filtered off and the solvents are evaporated at a temperature of less than 35° C. The residue (about 74 g) is flash-filtered through a bed of silica (200 g) with ethyl acetate/heptane (1:1). The fractions containing the product are concentrated to a solid mass (26 g, 90%). Following recrystallization from chloroform/heptane (1:3 150 mL), a tan solid is obtained, melting point 87° C. (21.9 g, 75%). The pyruvyl-glycine is recrystallized using any suitable procedure such as freeze drying, spray drying or microwave vacuum drying. This one-step synthesis presents several advantages: (a) the scavenging of the acid liberated during the pyruvylation of the amino acid derivative is only slightly exothermic, thus giving better control over the reaction and necessitating little cooling during the reaction,; (b) the by-product (i.e. chloropropanols) can easily be removed by evaporation, thus avoiding the aqueous elimination of the salts generated by other methods; and (c) the cost of propylene oxide is negligible as compared to traditional organic bases.

The invention will be better understood in view of the following examples which are illustrative only and should not be construed as limiting the claims of invention.

EXAMPLE 1—COMPARISON TESTING

The following study was designed to determine the efficacy of one pyruvate analog, pyruvyl-glycine, administered as a dietary supplement to rats.

Experimental groups were formed having 8 rats in each group. For one week prior to the beginning of the test period, the rats were housed in individual cages and provided a powdered controlled diet to acclimate the rats to their surroundings. Familiarization of the rats with the powdered diet was determined by consistent weight gain and feed intake for no less than four days. Group I consisted of rats receiving a diet of 26% protein, 12.1% fat, and 62% carbohydrate (total kcals) pair-fed according to the experimental group that consumed the least amount of food. Each of the diets except that fed to the control group featured a diet comprised of 6% pyruvate (by calories). Experimental group 1 consisted of rats that received the controlled diet with the 9% calcium pyruvate substituted for sucrose (by weight). Experimental group 2 consisted of rats that received the controlled diet with 7.2% pyruvamide substituted for sucrose (by weight). Experimental group 3 consisted of rats that received a controlled diet with 12.2% pyruvyl-glycine substituted for sucrose (by weight).

Food bowls for all 4 groups were replenished with the diets on a daily basis. Food consumption for the previous day and body weights of the rats were recorded, and the animals were pair-fed to the group consuming the least amount. The rats were maintained on their respective diets for eight days. Set forth below in Table II are the actual ingredients associated with each of the four test groups.

TABLE II

| DIET | Control | Calcium Pyruvate | Pyruvamide | Pyruvyl-glycine |
|---|---|---|---|---|
| Ingredient, g | | | | |
| Casein | 200 | 200 | 200 | 200 |
| Methionine | 3 | 3 | 3 | 3 |
| Starch | 250 | 250 | 250 | 250 |

TABLE II-continued

| DIET | Control | Calcium Pyruvate | Pyruvamide | Pyruvyl-glycine |
|---|---|---|---|---|
| Sucrose | 358 | 310 | 286 | 236 |
| Cellulose | 50 | 50 | 50 | 50 |
| Corn Oil | 50 | 50 | 50 | 50 |
| Vitamins | 10 | 10 | 10 | 10 |
| Choline | 2 | 2 | 2 | 2 |
| Salt Mix | 5 | 5 | 5 | 5 |
| Ca/PO4 | 72 | 30 | 72 | 72 |
| CaPyruvate | 0 | 90 | 0 | 0 |
| PyrAmide | 0 | 0 | 72 | 0 |
| PyrGlycine | 0 | 0 | 0 | 122 |
| TOTAL | 1000 | 1000 | 1000 | 1000 |

Figure 1:
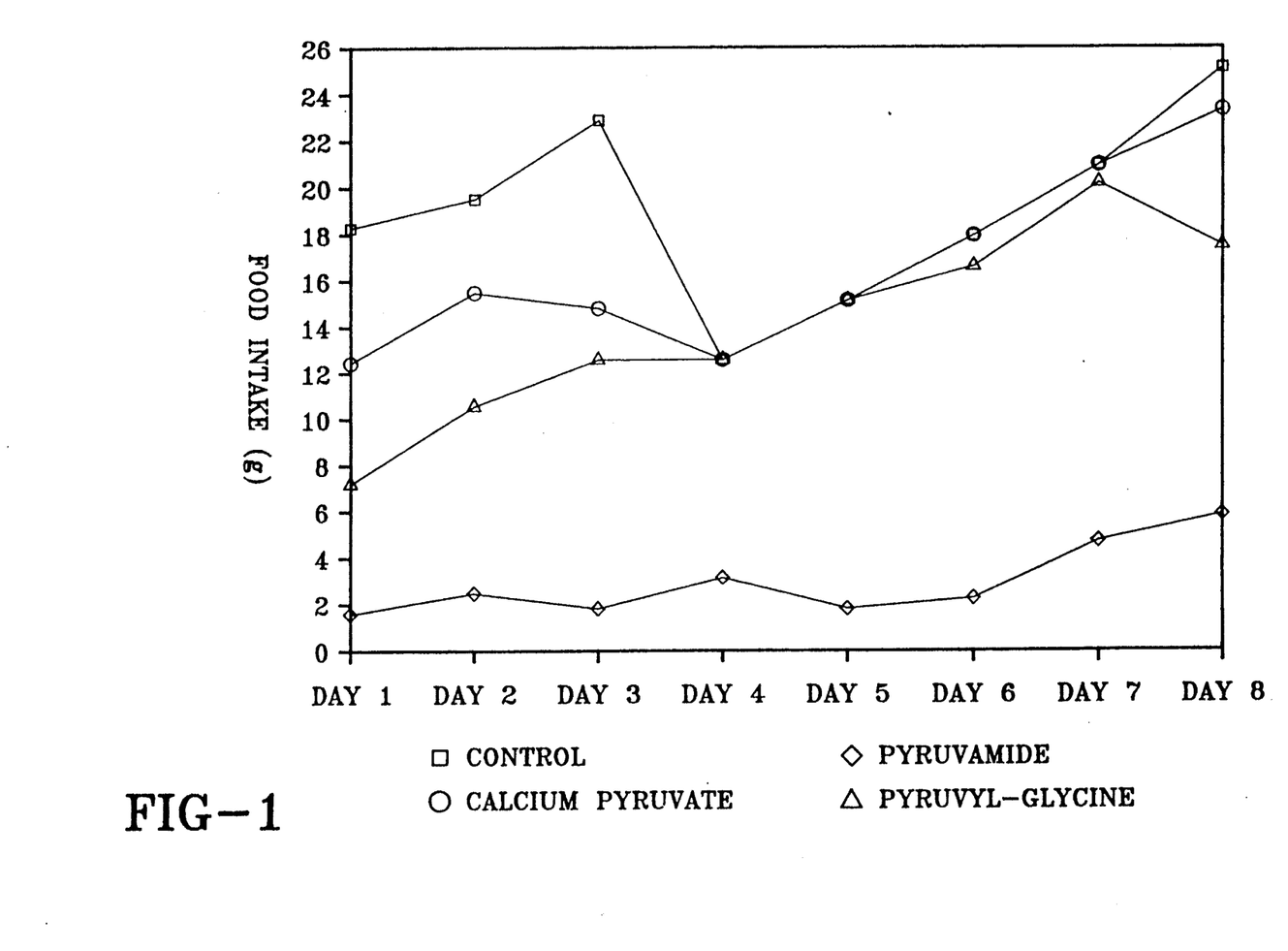
FIG. 1 is a graph illustrating the effect of the ingestion of pyruvate, and pyruvate analogs, using the method of this invention, on daily food intake.

As can be seen in FIG. 1, the food intake for the control group, the pyruvate group and the pyruvyl-glycine group all were somewhat similar especially through the time period of days 4–7. However, as has been discussed above, and as can be seen in FIG. 1, the daily food intake of the dietary treatment comprising pyruvamide was extremely insignificant.

Figure 2:
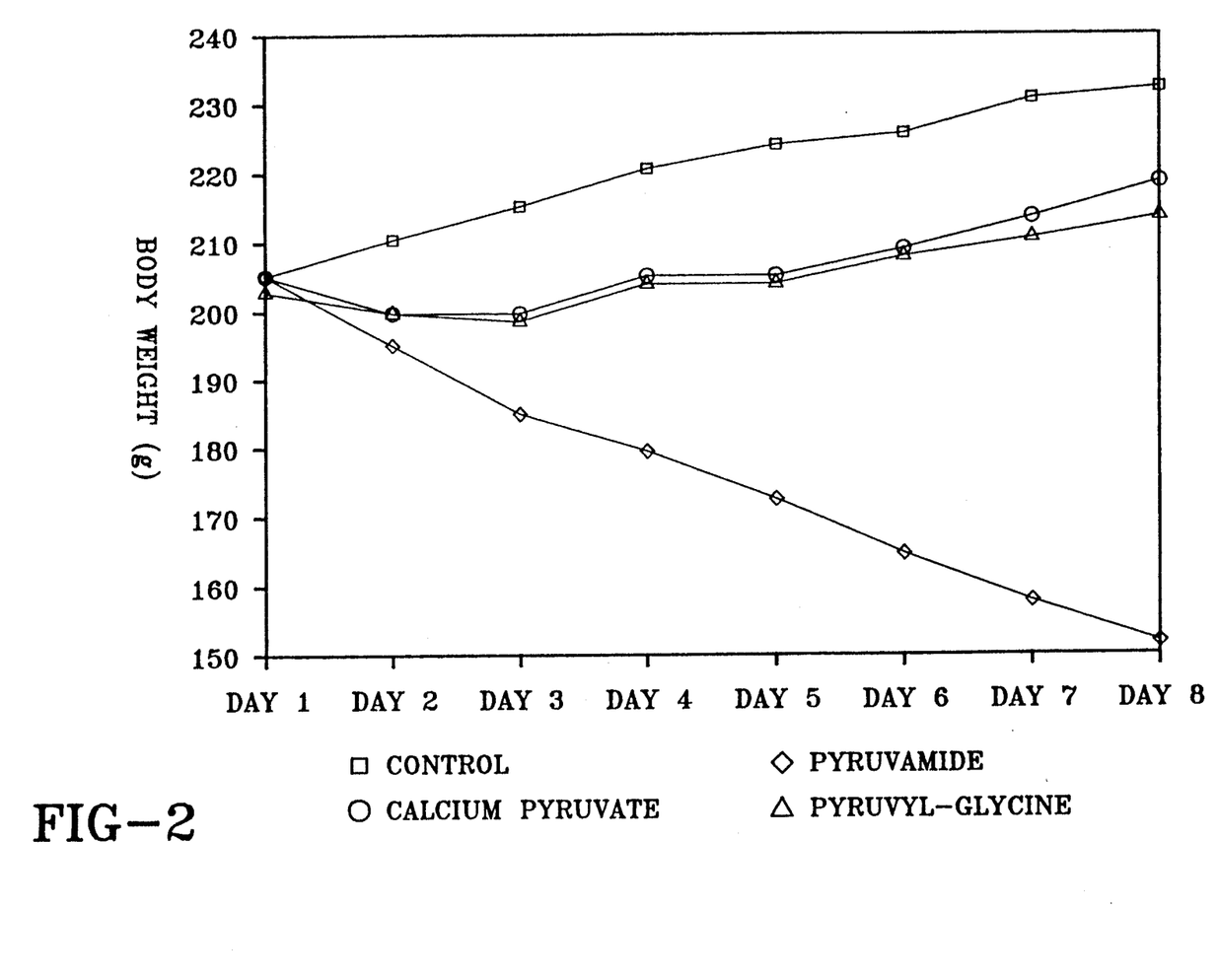
FIG. 2 is a graph illustrating the effect of the ingestion of pyruvate, and pyruvate analogs, using the method of this invention, on daily body weight.

As can be seen in FIG. 2, the body weight in grams of the control group increased from approximately 205 to approximately 230. Meanwhile, the pyruvate fed group exhibited a statistically significant smaller increase in body weight. However, as has been pointed out above, the use of the mineral salts of pyruvate in humans is precluded due to the high electrolyte levels produced. As can be seen, the pyruvyl-glycine fed test group also exhibited a lesser increase in body weight as compared to the control group. Finally, the pyruvamide test group displayed a sharp decrease in body weight. However, that was due to the insignificant amount of food consumed by these rats due to what was initially believed to have been a low tolerance to pyruvamide at these levels.

Based on these short duration test results, pyruvyl-glycine was found to have excellent potential as a substitute for pyruvate, because pyruvyl-glycine exhibited biological activity, exhibited no noticeable toxicity, and it eliminated the excessive mineral load associated with pyruvate salts while retaining chemical stability. In previous studies, pyruvyl-glycine has been shown to be as stable as the mineral salt of pyruvate in casein diets (less than 3% loss at 37° Centigrade over 5 days), while pyruvamide appeared more unstable (73% loss under similar conditions). Additionally, pyruvyl-glycine is also stable in simulated sterilization conditions (less than 5% loss at 125° Centigrade over 8 minutes) while the pyruvamide loss is higher (greater than 50% loss under similar conditions).

EXAMPLE 2—COMPARISON TESTING

The longer term effects of pyruvate and pyruvyl-glycine on feed intake and weight gain of the rats in the comparison test were investigated by extending the testing for the control group and the two groups with the pyruvate dietary supplement and the pyruvyl-glycine dietary supplement.

Beginning after the eighth day of the test, the three groups were each fed at a reduced level of 15 g per day. The results of this test are shown in Table III.

TABLE III

| | Control Group | Pyruvate Group | Pyruvyl-Glycine Group |
|---|---|---|---|
| Food Consumption, g | | | |
| Day 0–8 | 152.1 | 132.2 | 111.6 |
| Day 8–23 | 225 | 225 | 225 |
| Day 0–23 | 377.1 | 357.2 | 336.6 |
| Avg daily intake, g | 16.4 | 15.5 | 14.6 |
| Weight Gain, g | | | |
| Day 0–8 | 27.8 | 13.7 | 12.4 |
| Day 8–23 | 52.3 | 50.2 | 45.5 |
| Day 0–23 | 80 | 64 | 57.8 |
| Avg daily gain, g | 3.48 | 2.78 | 2.51 |
| Initial wt, g | 205.4 | 205.6 | 202.3 |
| Final wt, g | 285.5 | 269.6 | 260.1 |

Figure 3:
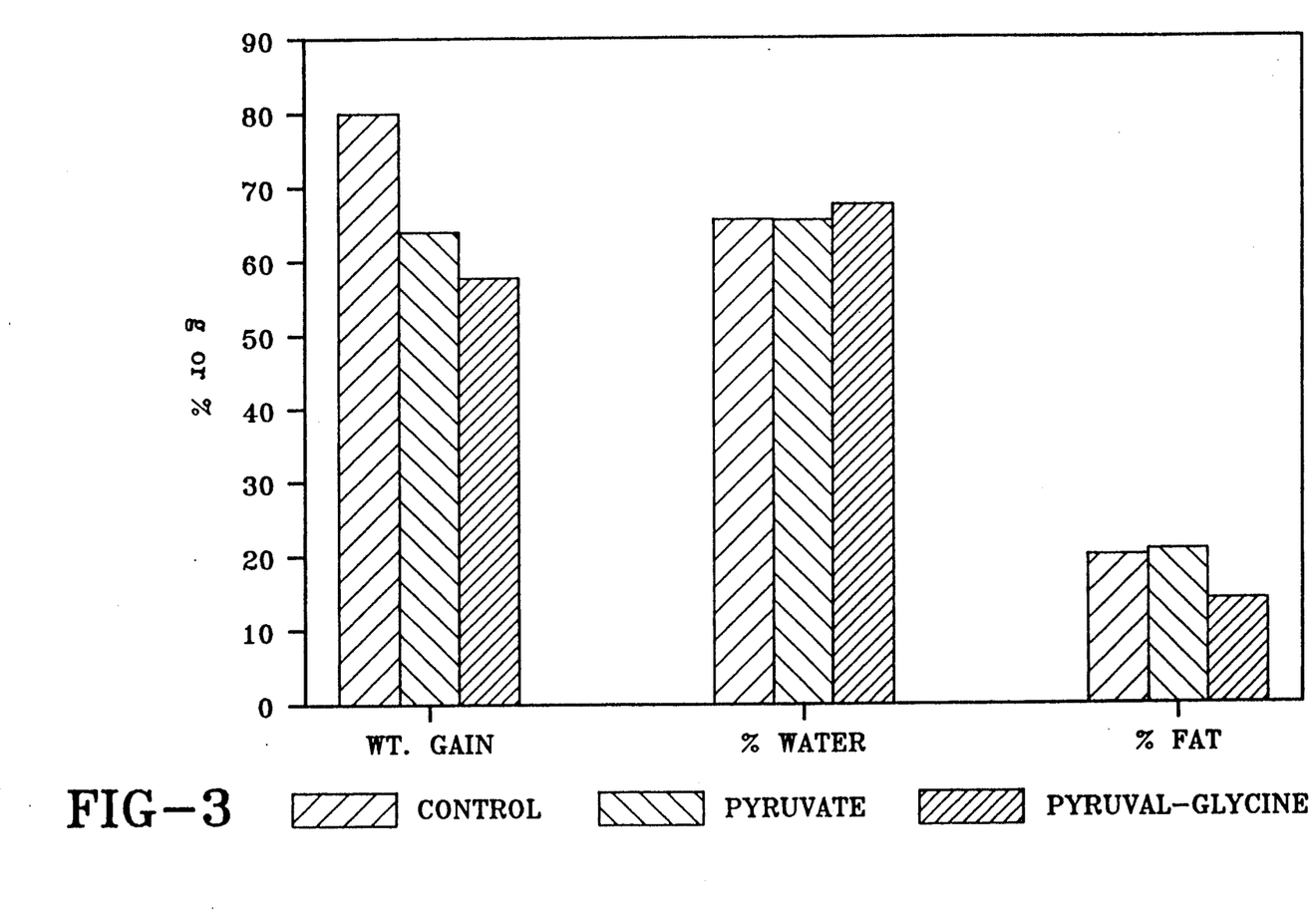
FIG. 3 is a graph illustrating the effect of pyruvate, and pyruvate analog, on weight gain, body water content and body fat content.

From day 8 to 23, weight gain was much more similar in each of the groups although the least in the pyruvyl-glycine group. Consumption of the pyruvyl-glycine dietary treatment resulted in a 12% lower carcass weight, a 50% decrease in retroperitoneal fat pad weight, and most strikingly, a lower percentage of total body fat, as shown in FIG. 3. In fact, in only 3 weeks, the group fed the dietary treatment comprising pyruvyl-glycine exhibited a 30% decrease in body fat content when compared to the other experimental groups.

Previous experiments have shown that the addition of pyruvate or pyruvate with DHA to the diet of rats causes a reduction in expected body weight gain. In this experiment, the addition of pyruvate to the diet had a suppressive effect on weight gain although no effect on carcass composition. Although pyruvate did not have a measurable effect on carcass consumption, pyruvyl-glycine had a dramatic effect on reducing the body fat content. This difference is remarkable given the relatively short length of the feeding trial. Despite the dramatic changes in fat content, lean body mass (protein) and ash levels were not adversely affected. In fact, as a percentage of body weight, protein and ash content were elevated in the pyruvyl-glycine fed group of rats.

The possible reasons for the enhanced effect of pyruvyl-glycine are not clearly understood. It is theorized that perhaps the enhanced effect could be the result of: (1) the addition glycine having a synergistic enhancement of the pyruvate effect; (2) the pyruvyl-glycine having a metabolic effect independent of either glycine or pyruvate; and/or (3) the pyruvate being stabilized by the linkage with glycine, such that the pyruvate is delivered to the target tissues at higher levels.

Figure 4:
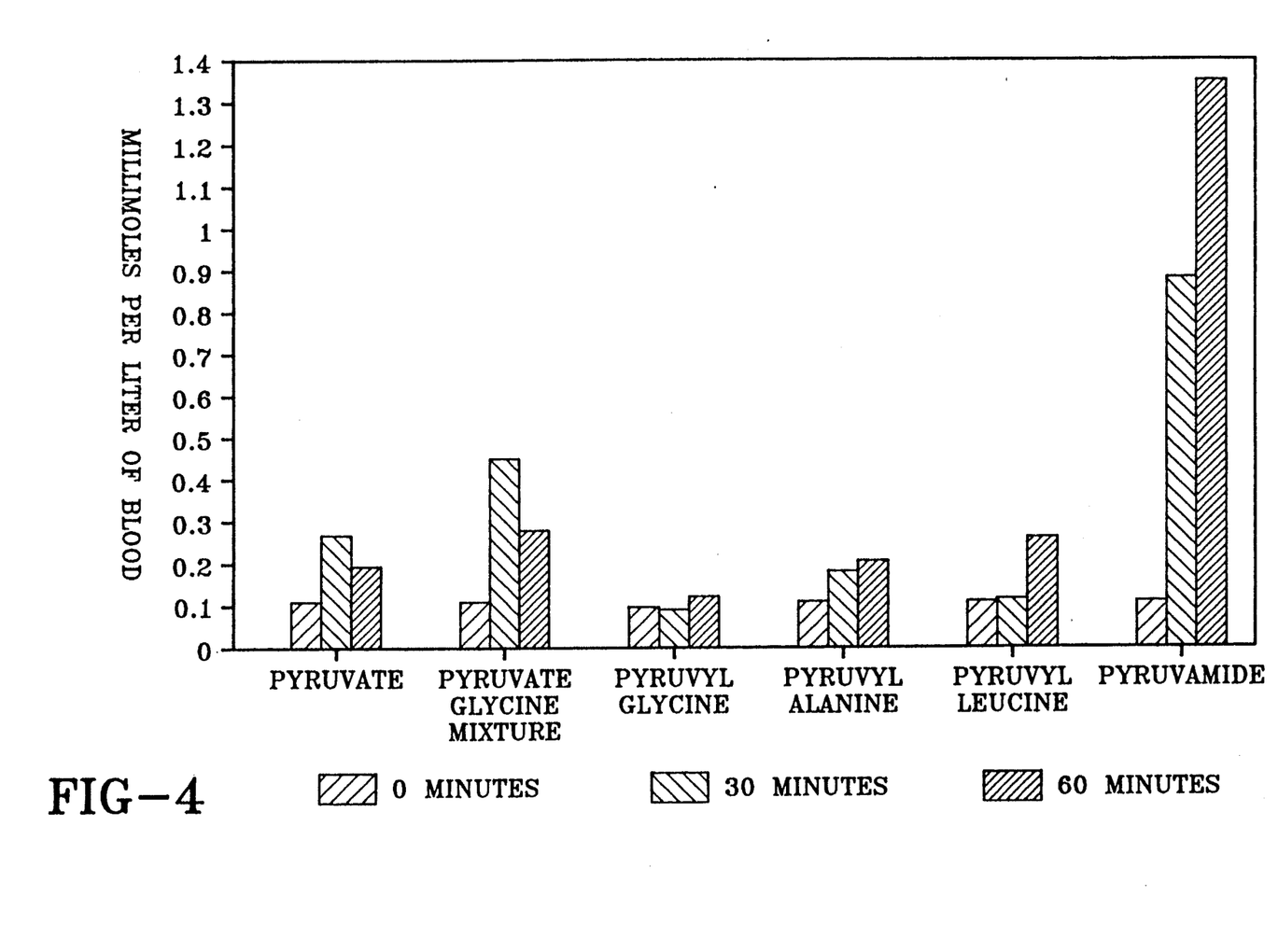
FIG. 4 is a graph illustrating the concentration of pyruvate in the body over time after gavage of various pyruvate precursors.

Additional tests were conducted to evaluate the actual effect of ingestion of non-salt pyruvate analogs on the pyruvate level in blood. FIG. 4 shows the level of pyruvate concentration in millimoles per liter of blood over a period of time for rats fed pyruvate, a pyruvate/glycine mixture, pyruvyl-glycine, pyruvyl-alanine, pyruvyl-leucine, and pyruvamide. It was expected that these tests would confirm the efficacy of pyruvyl-glycine as a pyruvate precursor.

As can be seen in FIG. 4, the administration of pyruvate caused the concentration of pyruvate in the blood to increase. Similarly, and for reasons still not fully understood, the oral ingestion of pyruvate with glycine resulted in a higher concentration of pyruvate ultimately evidencing itself in the blood. It was somewhat surprising therefore to see the change in the pyruvate level when pyruvyl-glycine was ingested and broke down to form pyruvate and glycine which could then be measured. Thus, it was found that pyruvyl-glycine caused a slight increase in pyruvate and a substantial increase in glycine, therefore it was an acceptable pyruvate analog, although it was perhaps not the best analog available. Subsequent tests with pyruvyl-alanine and pyruvyl-leucine showed that these two pyruvyl-amino acids were in fact capable of supplying greater amounts of pyruvate to the body over a lesser amount of time.

The level of pyruvate concentration in the blood following administration of pyruvamide was then tested. Surprisingly the pyruvate concentration experienced its most dramatic increases. As can be seen in FIG. 4, the pyruvate concentration after 1 hour was almost four times as high when compared with ingestion of the other analogs. Based on this development it was theorized that the apparent intolerance to pyruvamide in the earlier tests was caused not by an aversion to any ingestion of pyruvamide, but because the pyruvamide was converted far more quickly to pyruvate, therefore requiring far less total ingestion of the analog to obtain the desired result. Thus, a decrease in the amount of pyruvamide actually allowed to be ingested is now believed to provide the best solution to the problem.

EXAMPLE 3—COMPARISON TESTING

The following study was designed to determine the efficacy of one pyruvate analog, pyruvyl-glycine, administered to rats having problems with obesity and Type II diabetes (fatty Zucker rat). These rats were fed for 21 days diets identical as to those described in Example 1. These rats experience difficulty in controlling blood glucose levels so they must produce high amounts of insulin in order to keep blood glucose normal.

Figure 5:
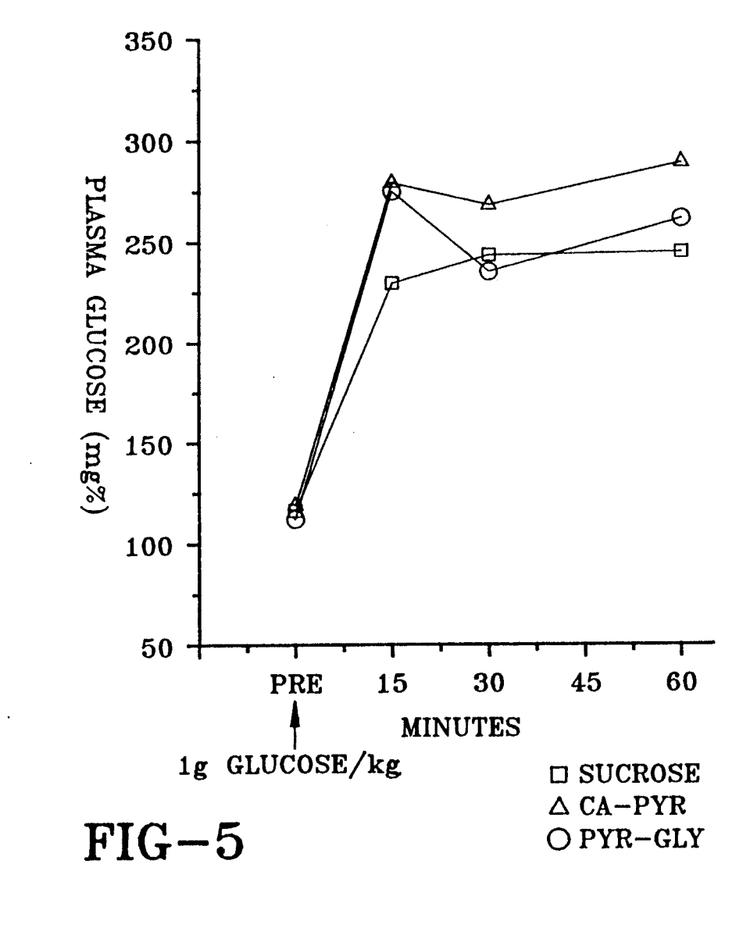
FIGS. 5 and 6 are graphs illustrating the effect of the ingestion of pyruvate, and pyruvate analogs, on glucose and insulin levels in fatty Zucker rats after a glucose tolerance test.
Figure 6:
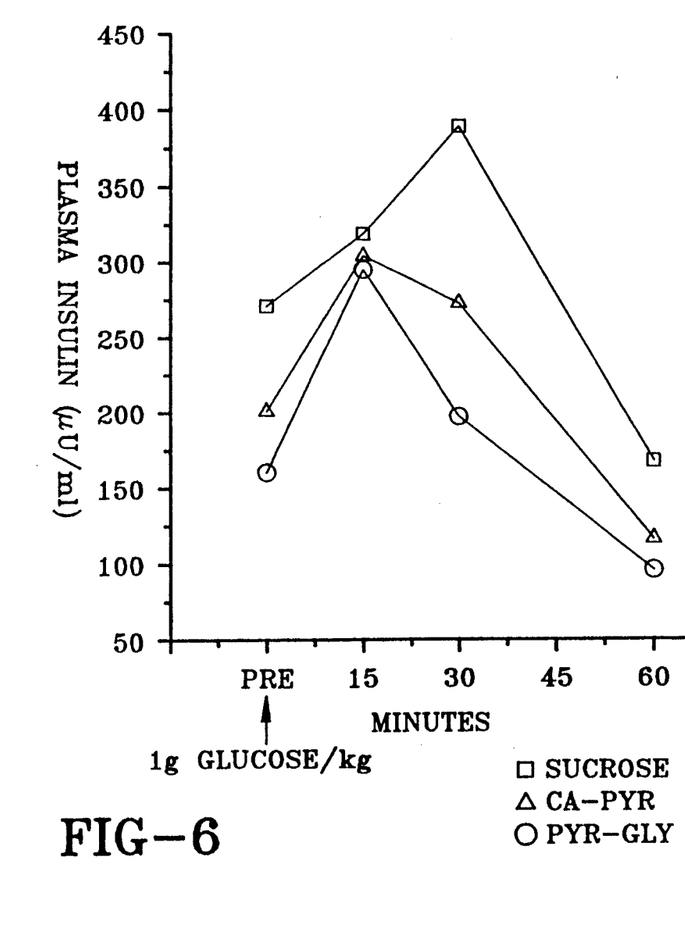

After 21 days of feeding the respective diets, the pyruvate-fed and the pyruvyl-glycine-fed rats had reduced fasting insulin levels, yet fasting blood glucose was not negatively affected. This is shown in FIGS. 5 and 6. A glucose tolerance test was then administered to these rats by gavaging 1 g glucose/kg body weight. The blood glucose was similar in all treatment groups but the insulin levels in the pyruvate fed group, and especially in the pyruvyl-glycine fed group, were lower than in the control fed group. This indicates that the rats fed pyruvate and pyruval-glycine result in reduced insulin resistance in these fatty Zucker rats.

The dietary supplement of this invention could be utilized in a complete nutritional, similar to ENSURE® which is a nutritional product distributed by Ross Laboratories, Columbus, Ohio, as a dietary supplement which could be added to a drink, or as a dietary supplement consumable in tablet form, as individual preference determines. Other methods of administration could be via enteral, parenteral, or other oral delivery systems. Similarly, the preferable level of usage would be anywhere from 0.5% to 20% by weight of the diet, dependent upon the results desired.

While the method for administering pyruvate and more particularly the methods of synthesizing non-salt precursors to pyruvate herein described constitute preferred embodiments of this invention, it is to be understood that the invention is not limited to this precise form of method and that changes may be made therein without departing from the scope of the invention which is defined in the appended claims.

What is claimed is:

1. A method of synthesizing the pyruvate precursor pyruvamide comprising the steps of:
   (a) reacting sodium pyruvate with a substance selected from the group consisting of thionyl chloride and oxalyl chloride to yield pyruvyl chloride; and
   (b) reacting the pyruvyl chloride with 1,1,1,3,3,3-hexamethyldisilazane at a temperature of 0°–40° Centigrade, followed by treatment with methanol in the presence of a solvent to generate pyruvamide.

2. A method of synthesizing the pyruvate precursor pyruvamide according to claim 1 wherein said solvent is selected from the group comprising dichloromethane, tetrahydrofuran, acetonitrile, dioxane and dimethylformamide.

* * * * *

UNITED STATES PATENT AND TRADEMARK OFFICE
CERTIFICATE OF CORRECTION

PATENT NO.  :   5,312,985
DATED       :   May 17, 1994
INVENTOR(S) :   M. Dhaon, J. Houbion It is certified that error appears in the above-identified patent and that said Letters Patent is hereby corrected as shown below:

On the cover page the title of the invention should be corrected to be --METHOD OF SYNTHESIZING THE PYRUVATE PRECURSOR PYRUVAMIDE--.

Signed and Sealed this

Sixth Day of September, 1994

Attest:

BRUCE LEHMAN

*Attesting Officer*    *Commissioner of Patents and Trademarks*